United States Patent [19]

Tanswell et al.

[11] Patent Number: 4,624,930
[45] Date of Patent: Nov. 25, 1986

[54] IMMUNOCHEMICAL PROCESS

[75] Inventors: Paul Tanswell, Laupheim/Obersulmetingen; Manfred Baier, Pöcking-Possenhofen; Helmut Lenz, Tutzing, all of Fed. Rep. of Germany

[73] Assignee: Boehringer Mannheim GmbH, Mannheim-Waldhof, Fed. Rep. of Germany

[21] Appl. No.: 508,258

[22] Filed: Jun. 27, 1983

[30] Foreign Application Priority Data

Jul. 5, 1982 [DE] Fed. Rep. of Germany ....... 3225027

[51] Int. Cl.⁴ .......................................... G01N 33/543
[52] U.S. Cl. ..................................... 436/500; 436/512; 436/518; 436/524; 436/528; 436/808; 436/813; 436/817; 436/823; 436/824; 435/7
[58] Field of Search ............... 436/500, 501, 504, 512, 436/518, 524–534, 536, 538–542, 800, 804, 808–811, 813, 815, 817, 823–824; 435/4, 7; 260/112 R; 206/569

[56] References Cited

U.S. PATENT DOCUMENTS

| | | | |
|---|---|---|---|
| 4,048,298 | 9/1977 | Niswender | 436/540 |
| 4,098,876 | 7/1978 | Piasio et al. | 436/540 |
| 4,200,436 | 4/1980 | Mochida et al. | 435/7 |
| 4,235,869 | 11/1980 | Schwarzberg | 436/512 |
| 4,281,061 | 7/1981 | Zuk et al. | 435/7 |
| 4,287,300 | 9/1981 | Gibbons et al. | 435/5 |
| 4,298,593 | 11/1981 | Ling | 436/512 |
| 4,343,896 | 8/1982 | Woltees et al. | 435/7 |
| 4,353,982 | 10/1982 | Gomez et al. | 435/7 |
| 4,376,110 | 3/1983 | David et al. | 436/513 |
| 4,397,960 | 8/1983 | Moussebois | 436/512 |
| 4,469,787 | 9/1984 | Woods et al. | 435/7 |
| 4,469,796 | 9/1984 | Axen et al. | 435/7 |
| 4,471,058 | 9/1984 | Smith et al. | 435/7 |

FOREIGN PATENT DOCUMENTS

| | | |
|---|---|---|
| 1123336 | of 0000 | Canada . |
| 0008473 | of 0000 | European Pat. Off. . |
| 0064318 | of 0000 | European Pat. Off. . |
| 2084317 | of 0000 | United Kingdom . |
| 2074727 | of 0000 | United Kingdom . |

Primary Examiner—Charles F. Warren
Assistant Examiner—M. Moskowitz
Attorney, Agent, or Firm—Felfe & Lynch

[57] ABSTRACT

A process for determining the presence of polyvalent antigens by incubation with three receptors is presented. In addition, a kit for carrying out this process is provided as well. One of said receptors is bound to a solid support and the other two, in solution, derive from the same animal species.

14 Claims, 3 Drawing Figures

IMMUNOCHEMICAL PROCESS

The present invention is concerned with an immunochemical process for the determination of one at least bifunctional ligand (antigen) in a liquid sample.

The sensitive determination of polyvalent antigens (peptides, proteins) with the use of two antibodies which are directed against different antigen determinants is known as the 2-site immunoradiometric or immunoenzymometric assay and is described, for example in J. Clin. Chem. Clin. Biochem., 18, 197–208/1980. The most usual manner of carrying out this known process of determination is first to incubate the antigen to be determined with a first antibody, which is present in the solid phase by binding to an appropriate carrier material, for example sepharose, agarose, synthetic resin test tubes or the like. During this first incubation, the first antibody, which as a rule must be present in large excess, binds with one of the antigen determinan of the antigen to be determined. The sample liquid is then usually separated from the solid phase in order to exclude disturbances due to non-specific substances, such as human serum proteins, or due to cross-reacting antigens in the subsequent second incubation. A definite amount of a second marked antibody is then incubated in the liquid phase with the solid phase. The specificity of the second antibody is thereby preferably selected in such a manner that it is directed against another determinant of the antigen to be determined in order to exclude a competition between the two antibodies for the same binding site on the antigen to be determined since the test sensitivity would hereby be impaired.

During this second incubation, the marked second antibody, which is also usually present in excess, reacts with all binding sites on the molecule of the antigen to be determined. After the second incubation, the activity of the marking substance can be measured either in the solid phase or in the supernatant. The measurement thereby usually takes place on the solid phase after washing out of the liquid phase. In the most favourable case, the activity determined is almost proportional to the amount of the antigen to be determined.

This 2-step sandwich process has the advantage that possibly cross-reacting antigens are already removed in the first phase separation. This is of especial importance in the case of test systems in which the two antibodies must indeed possess a different specificity because of sensitivity requirements. In this case, the high requirements demanded of the specificity apply to only one of the two antibodies but the other one must then not be absolutely specific towards cross-reacting antigens.

However, this process suffers from three important disadvantages:

1. In the first incubation step, one reactant is present in solid phase and the other in solution. The velocity constant of the reaction is thus smaller than it would be were both reaction components (antigen and first antibody) present in solution. However, it is necessary to incubate until all antigen molecules present are bound to the solid phase since non-bound antigen would be removed in the case of the phase separation and would thus result in a falsification of the result.
2. The binding of a bindable antibody specific for the antigen on to a solid phase requires, because of the low binding yields, relatively large amounts of the first antibody, which is usually a very expensive substance, especially when, for reasons of specificity, the antiserum must be obtained from small animals, such as rabbits, guinea pigs or the like. Furthermore, in the case of the binding reaction to the solid phase, affinity impairments on the antibody can result, which have a disadvantageous effect on the sensitivity.
3. The obtaining of two antibodies of different specificity against the same antigen is, as a rule, laborious and frequently only possible to a limited extent, for example by immunising two different animal species or by attempting to separate the antibody populations from one animal by immune adsorption on to suitable fragments of the antigen to be determined.

Various attempts have already been made to overcome the above deficiencies. Thus, according to U.S. Pat. No. 4,098,876, the first incubation is carried out with isotope-marked, dissolved antibody. Only thereafter is the solid phase-bound antibody added thereto and the second incubation carried out. In this case, only one phase separation is necessary, which results in a certain increase of the sensitivity and of the practicability. However, the problem of specificity remains unsolved since both antibodies must be directed highly specifically against the antigen. Furthermore, in the presence of comparatively large amounts of cross-reacting antigens, the apparent concentration of the antigen to be determined is, in the case of a possible non-specificity of the second antibody, increased and in the case of non-specificity of the first antibody is lowered.

Federal Republic of Germany Patent Specification No. 29 25 565 describes a process in which the first antibody present in the solid phase and the marked, dissolved second antibody are simultaneously incubated with the antigen. There here exists the same problem as in the case of the above-mentioned process. Furthermore, the second and third disadvantages described above for the basic process remain unsolved.

Japanese Patent Specification No. 123,802 of the Oct. 6, 1978, describes a process in which a solid phase antibody is used which is specifically directed against the second antibody, which is capable of binding with the antigen to be bound. In this case, the binding of an antibody directed against the antigen to the solid phase is avoided. However, the sensitivity is reduced since there is used only a single antibody capable of binding specifically with the antigen. The detection of the concentration of the antigen to be determined takes place via the competitive reaction between the antigen and a definite amount of isotopemarked antigen with the specific antibody.

Finally, from Clin. Chem., 27/6, 823–827/1981, there is known a radiometric method of determination for creatine kinase MB-isoenzyme in which, in a first incubation step, the antigen is reacted simultaneously with an unmarked and with a marked antibody of differing specificity and from differing animal species. In the second step, there is then added an antibody, present in solid phase, with specificity against the unmarked antibody of the first incubation step. Here again, the disadvantage of this process is that there are needed two different antibodies specific for the antigen and three different animal species.

Therefore, it is an object of the present invention better to avoid one or more of the above-described disadvantages of the basic process than the previously known processes.

Thus, according to the present invention, there is provided a process for the determination of a polyvalent antigen by incubation with three different receptors, the first and third of which are present in liquid phase and are capable of binding with the antigen and the second receptor is present in solid phase and is capable of binding with the first receptor and the third receptor carries a marking and does not cross-react with the first and second receptors, separation of the solid phase from the liquid phase and measurement of the marking in one of the phases, wherein the antigen is simultaneously incubated with all three receptors or with the first and second receptor, whereafter the phases are separated, the solid phase is possibly incubated with the third receptor and the phases are again separated.

As receptors in the scope of the present invention, there are used either specifically bindable complete antibodies, antibody fragments or conjugates of antibodies or antibody fragments with haptens. As first receptor, there is preferably used a complete antibody or an antibody covalently bound with a hapten.

As second receptor, there is preferably used an antibody which is capable of binding with only a part of the first receptor and especially preferably an antibody which is capable of binding with the Fc part of the first receptor. Alternatively, as second receptor, there can also be used an antibody which is capable of specifically binding with the hapten part of the first receptor or with the Fab part or with the total first receptor.

The third receptor, which must not cross-react with the second receptor, can be an antibody capable of binding with the antigen, which is obtained from an animal species different from that from which the first receptor is obtained.

However, it is preferred to use a third receptor which consists of a part, for example a fragment, of the first receptor and, therefore, is obtained from the same animal species as the first receptor. This also applies when the first receptor consists of an antibody which carries a hapten and the second receptor is only capable of binding with this hapten. The third receptor is especially preferably a Fab fragment of the first receptor. Alternatively, as third receptor, there can also be used an antibody which originates from the same animal species as the second receptor. Both alternatives have the advantage that only two animal species are required for the three receptors. When the second receptor is only capable of binding with the hapten, then only one animal species is required for all three receptors.

The third receptor, which is used in known amount, is marked in known manner. The marking is preferably carried out by coupling with an enzyme or with a fluorescing, chemiluminescing or radioactive substance. Processes for marking such receptors are well known, for example from Clin. Chim. Acta, 81, 1–40/1977, and do not require further explanation here.

The process according to the present invention can be carried out in such a manner that the sample containing the antigen to be determined, which is at least divalent, is incubated with all three receptors simultaneously. In this case, after the incubation, the solid and liquid phases are separated and the amount of marked third receptor is determined either in the liquid phase or preferably in the solid phase.

However, according to a preferred embodiment of the process of the present invention, the antigen-containing sample is first incubated with the first and second receptors, whereafter the phases are separated and only the separated solid phase is incubated with the third receptor in a second incubation step. Thereafter, the solid phase is again separated from the liquid phase and, as described above, the amount of marked third receptor in one of the phases is measured. In the case of this two-step incubation, it is sufficient when only the first or the third receptor is specifically bindable with the antigen and the other receptor can also be capable of binding with other antigens, i.e. it can be non-specific. In the case of the one-step incubation, i.e. with the simultaneous use of all three receptors, the first and the third receptor must be specifically bindable.

The binding of the second receptor, present in solid phase, to an insoluble carrier material can be carried out by the usual methods known for fixing biologically-active proteins on to solid carrier substances. Not only a covalent but also an adsorptive binding can be used. However, because of the hereby achievable higher yields and the simplified method of working, it is preferred solely to use an adsorptive binding, for example on to a synthetic resin. Reagent vessels of polystyrene and similar synthetic resins, which are adsorptively coated on the inner surface with the second receptor, have proved to be especially preferable. The first and possibly the second incubation is then carried out in these test tubes or in containers of some other shape and, for the phase separation, it is sufficient to remove the liquid phase from the test tube, for example by sucking it out or the like. After washing the test tube, the measurement of the marking therein can then be carried out immediately, especially when marking has been carried out with an enzyme. It is then sufficient simply to measure the activity of the marking enzyme, for example peroxidase or $\beta$-galactosidase, in the manner generally known for this purpose. The measured enzyme activity is then a measure for the amount of polyfunctional antigen to be determined. However, as solid phase carrier for the second receptor, there can also be used particulate substances, for example ion exchangers, molecular sieve materials, glass bodies, synthetic resin tubes and the like.

If the marking takes place not with an enzyme but with a radioactive substance, an isotope, a fluorescing or a chemiluminescing substance, the determination is here also carried out according to one of the methods well known for this purpose. Therefore, a description of these methods of measurement is here unnecessary.

Surprisingly, we have found that, according to the process of the present invention, there is achieved a sensitivity which is distinctly greater than in the case of the usual 2-step sandwich method. Furthermore, the first receptor can be used in a substantially lower concentration than would be possible were the first receptor present in solid phase.

If, according to the preferred embodiment of the process of the present invention, there is used a second receptor directed against the Fc part of the first receptor or against the hapten which is coupled with the first receptor, then a further increase of the sensitivity can hereby be achieved since a possible steric hindrance of the binding reaction of the antigen with the binding site of the first receptor is avoided. This is a particular advantage when antigens with especially low concentrations have to be determined, such as is the case, for example, in the determination of thyreotropin in serum.

If, according to the process of the present invention, as third receptor there is used a Fab fragment of the first receptor, then, as can readily be seen, receptor 1 and receptor 3 preferably originate from the same animal species since receptor 2 certainly only displays determinants against the Fc part of the antibody or against the hapten coupled with this.

The present invention also provides a dry reagent for the determination of a polyvalent antigen, wherein it contains two different soluble receptors capable of binding with the antigen, one of which carries a marking, and an insoluble third receptor capable of binding with the unmarked soluble receptor, the marked receptor containing a part of the first receptor or originating from the same animal species as the insoluble third receptor, the insoluble receptor and the unmarked soluble receptor being present physically separated.

The physical separation can take place, for example, in that the insoluble receptor and the unmarked soluble receptor are lyophilised stepwise one after the other, with the application of an inert intermediate layer which, for example, can consist of sugar and is applied to the layer of the first lyophilised receptor. Thus, for example, it is possible first to lyophilise the second receptor on the inner wall of a synthetic resin test tube, to lyophilise thereover an inert intermediate layer, for example of cane sugar, and then to lyophilise thereon the unmarked soluble receptor. The third, marked, soluble receptor can thereby be added in admixture with the first receptor or separate therefrom. Apart from carbohydrates, as intermediate layer there can also be used a readily soluble polymer, for example in the form of a film of a water-soluble polymer.

The present invention can be used for the determination of all antigens with at least two antigen determinants. Examples thereof include thyreotropin (TSH), α-1-foetoprotein (AFP), hCG, carcinoembryonic antigen, luteinising hormone (LH), follicle-stimulating hormone (FSH), $\beta_2$-microglobulin, acidic prostrate phosphatase, prolactin, ferritin and insulin.

In the case of the present invention, receptor 1 can react homogeneously with the antigen. Consequently, this reaction has a higher velocity constant than in the case of using a solid phase-bound first receptor. Since antibody losses in the case of fixing on to the solid phase are avoided, the amount of first receptor can be further reduced.

In contradistinction to the process described in Clin. Chem., 27/6, 823–827/1981, it is also not necessary to obtain the first and the third receptor from two different animal species which must also be so chosen that receptor 2 only reacts with receptor 1 but not with receptor 3.

The obtaining of the antibody for receptor 1 and for receptor 3 from the same animal species also makes it possible to employ large animals for obtaining the antiserum.

The above-described advantages also apply in the case of carrying out the process according to the present invention with only one incubation step. In the latter case, however, specificities cannot be achieved which are just as great as in the case of the preferred embodiment with two incubation steps.

Finally, according to the present invention, the sensitivity is also increased. Thus, for TSH there is found a sensitivity of less than 40 pg./ml. (1 $\mu U \triangleq 170$ pg./ml.), whereas in the case of the 2 site assay (sandwich process) it is above 100 pg./ml.

The following Examples are given for the purpose of illustrating the present invention:

EXAMPLE 1

Determination of Thyreotropin (TSH)

Into plastics test tubes which are adsorptively coated with about 100 ng. anti-rabbit-Fcγ from sheep, obtained by immunising with Fcγ fragments from rabbit IgG (the coating method used corresponds to the usual, known methods), there are pipetted 200 μl. of a sample or of a standard, containing increasing or unknown amounts of thyreotropin and 1000 μl. of a solution consisting of buffer A and 20 ng./ml. of anti-TSH-antibodies from the rabbit (Buffer A: 10 mM monosodium dihydrogen phosphate/monopotassium dihydrogen phosphate of pH 7.0).

The solution is incubated for 12 to 16 hours at ambient temperature. Thereafter, the contents of the tubes are sucked out, the tubes are washed once with 0.9% aqueous sodium chloride solution and subsequently 1000 μl. of conjugate solution, consisting of an aqueous solution of anti-TSH antibodies from sheep to which peroxidase is covalently bound in a peroxidase concentration of 67 mU/ml., are pipetted into the test tubes.

After an incubation period of 2 hours at ambient temperature, the contents of the test tube are sucked out, the tube is washed and subsequently 1000 μl. of a reagent for the detection of peroxidase activity are pipetted into the test tube.

Figure 1:
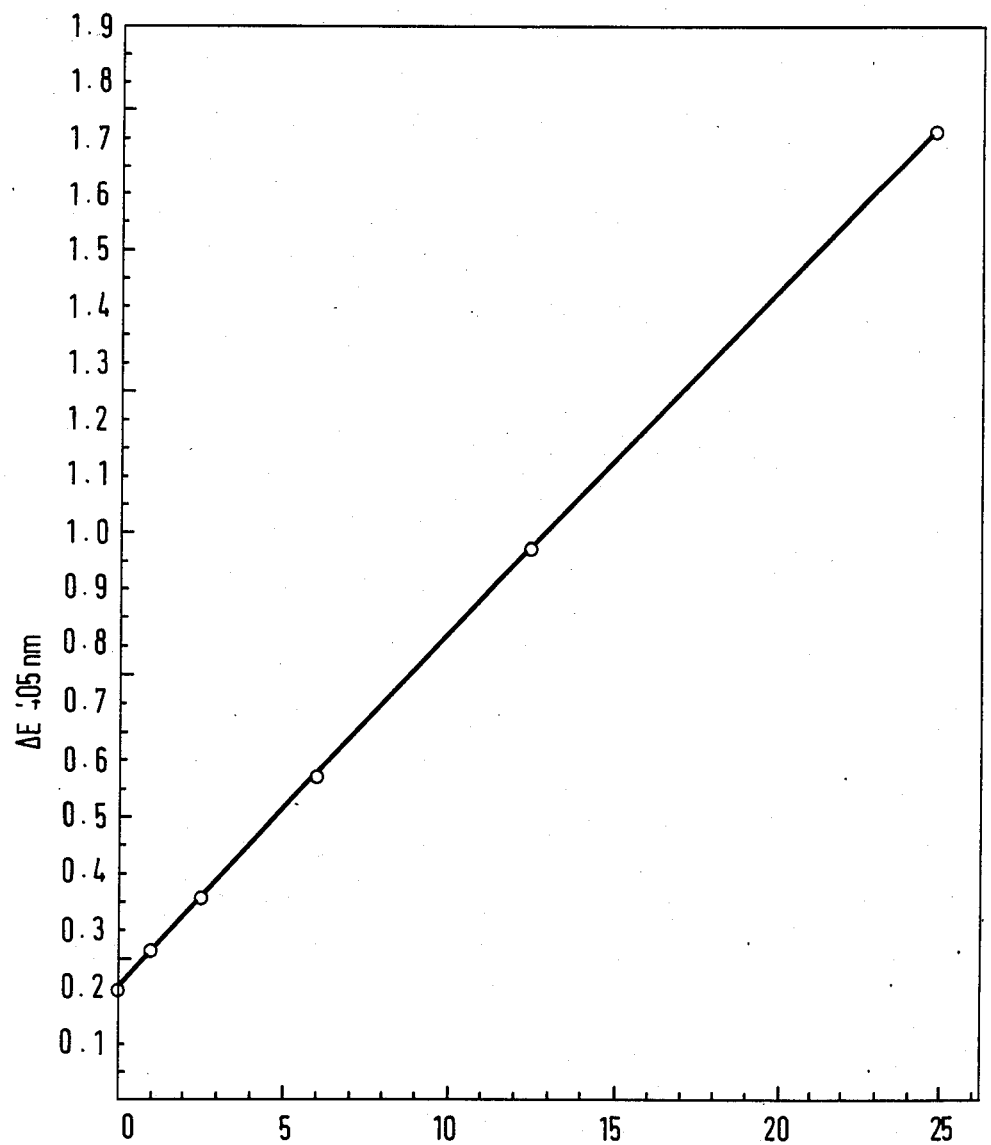
FIG. 1 is a calibration curve showing extinction at 405 mm versus concentration of thyreotropin (TSH).

As reagent, there is used 2,2'-azino-di-(3-ethylbenzthiazoline-6-sulphonate) (ABTS) (1.8 mM, perborate 3.3 mM in phosphate-citrate buffer, 100 mM; pH 4.4). After a further incubation period of 1 hour at ambient temperature, the contents are transferred to a cuvette and the extinction is measured at 405 nm against reagent as a blank. From the extinction obtained, there is produced the calibration curve shown in FIG. 1 of the accompanying drawings.

The covalent bonding (coupling) of peroxidase to antibody is carried out according to the method of M. B. Wilson and Paul K. Nakane, described in "Recent Developments in the periodate method of conjugating horse radish peroxidase (HRPO) to antibodies", 1978, Elsevier/North-Holland Biomedical Press, pages 215–224 in "Immunofluorescence and related staining techniques".

EXAMPLE 2

Determination of α1-foetoprotein (AFP)

200 μl. of sample or of standard containing increasing amounts of AFP are pipetted with 30 ng. anti-AFP antibodies from rabbits, dissolved in 1000 μl. phosphate buffer (100 mM; pH 6.8), into the same test tubes as are used in Example 1 (containing Fc fragments of rabbit IgG).

After incubating for 2 hours at ambient temperature, the contents of the tubes are sucked out, the tubes are washed and 1000 μl, conjugate, consisting of anti-AFP antibodies from sheep coupled to peroxidase (according to the method of Nakane), are pipetted into the test tubes.

After a further period of incubation of 2 hours at ambient temperature, the contents of the tubes are again sucked out, the tubes are washed and the substrate solution for the detection of the peroxidase activity fixed on to the test tube wall is pipetted in. After an incubation period of 1 hour, the adsorption in measured in a photometer at 405 nm.

Figure 2:
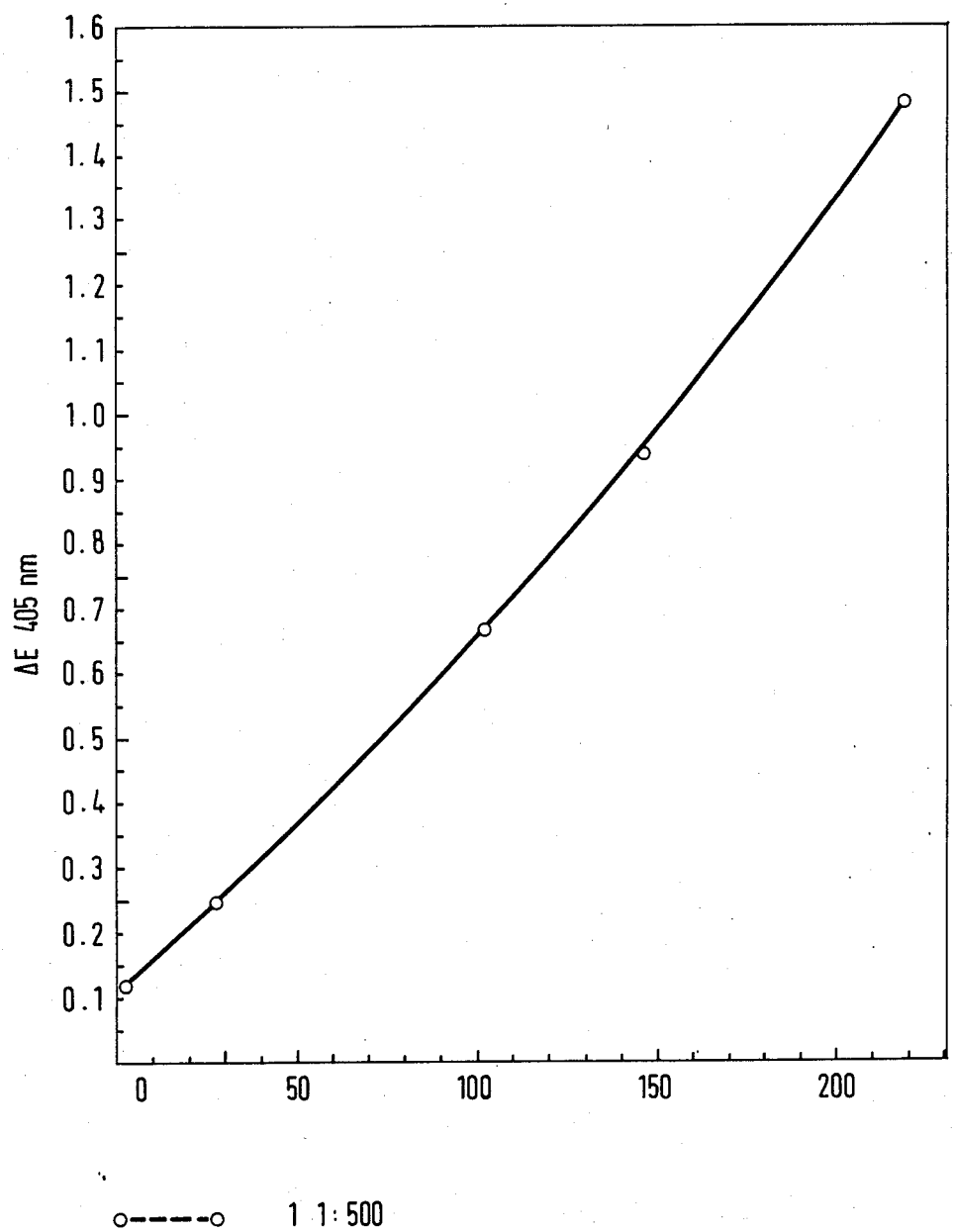
FIG. 2 is similar to FIG. 1, but is for alpha 1-foetoprotein (AFP).

Evaluation takes place via the calibration curve illustrated in FIG. 2 of the accompanying drawings, as described in Example 1.

EXAMPLE 3

Determination of α1-foetoprotein

In this embodiment, test tubes are used which are adsorptively loaded with anti-digoxin antibodies from rabbits (100 ng. anti-digoxin antibodies).

As antibody 1, there is used a conjugate of digoxin and anti-AFP antibodies from sheep (20 ng./ml.). The preparation of the conjugate is carried out in the manner described in Federal Republic of Germany Patent Specification No. 25 37 129.

Figure 3:
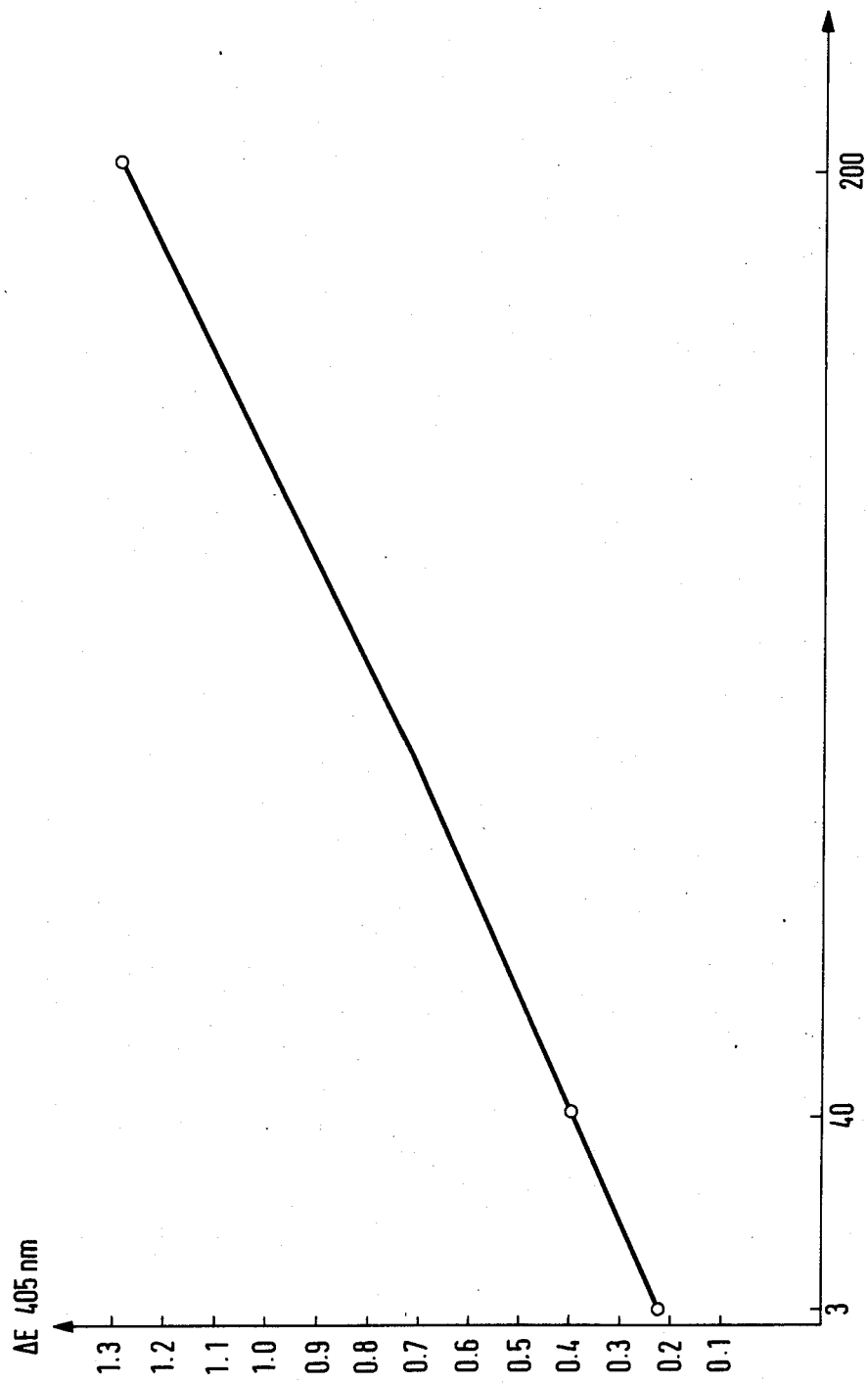
FIG. 3 is similar to FIG. 2 but a different procedure is used for determining the AFP.

Otherwise, the manner of carrying out corresponds to Example 2. The calibration curve obtained is shown in FIG. 3 of the accompanying drawings.

We claim:

1. A process for the determination of a polyvalent antigen which comprises:

incubating a sample containing polyvalent antigen with three different receptors, said first and third receptors being in a liquid phase and comprising an antibody or fragment thereof, wherein said antibodies or fragments thereof derive from the same species, said second receptor being present in a solid phase, the first and third receptors specifically binding to the antigen and said second receptor specifically binding with the first receptor, said third receptor further comprising a marking and not cross-reactive with said first and second receptors;

said incubation taking place under conditions favoring formation of antigen receptor complexes, and;

separating the liquid and solid phases following complex formation, and measuring the amount of labeled receptor in either the liquid or solid phase.

2. Process according to claim 1, wherein an antibody is used as the first receptor.

3. Process according to claim 2, wherein an antibody covalently bound with a hapten is used as the first receptor.

4. Process according to claim 2, wherein a second receptor is used which specifically binds to a part of the first receptor.

5. Process according to claim 3, wherein a second receptor is used which specifically binds with the $F_c$ part or the hapten part of the first receptor.

6. Process according to claim 2, wherein a separate molecule which is identical to a part of the first receptor is used as the third receptor 7. Process according to claim 6, wherein said third receptor is a separate molecule which is identical to a Fab fragment of the first receptor.

8. Process according to claim 1 wherein said third receptor is an antibody which originates from the same animal species as the second receptor.

9. Process according to claim 8, wherein all three receptors compromise antibodies or fragments thereof which originate from the same animal species.

10. Process according to claim 1 wherein said third receptor is marked with an enzyme or with a fluorescing, chemiluminescing or radioactive substance.

11. The process of claim 1 wherein the antigen is incubated simultaneously with all three receptors.

12. The process of claim 1 wherein the incubating step comprises incubating the antigen with the first and second receptor, whereafter the solid and liquid phases are separated and the solid phase is incubated with the third receptor.

13. A kit for the determination of a polyvalent antigen comprising first and third different soluble receptors which specifically bind to said antigen, said third receptor carrying a marking, and an insoluble second receptor which specifically binds to said first receptor, wherein said marked, soluble third receptor is a separate molecule identical to a part of said unmarked soluble first receptor and is derived from the same animal species as said first receptor, wherein said three receptors are present in amounts sufficient to determine the polyvalent antigen.

14. A kit as in claim 13, wherein said first and third receptors comprise an antibody or antibody fragment derived from the same animal species, and said third receptor not cross reacting with the first and second receptors.

* * * * *